United States Patent [19]

Nichols

[11] Patent Number: 4,657,548

[45] Date of Patent: Apr. 14, 1987

[54] DELIVERY SYSTEM FOR IMPLANTATION OF FINE PARTICLES IN SURGICAL PROCEDURES

[75] Inventor: Joseph Nichols, Princeton, N.J.

[73] Assignee: Helitrex, Inc., Princeton, N.J.

[21] Appl. No.: 858,041

[22] Filed: May 1, 1986

Related U.S. Application Data

[63] Continuation of Ser. No. 649,281, Sep. 11, 1984, abandoned.

[51] Int. Cl.$^4$ .............................................. A61F 1/00
[52] U.S. Cl. .................................. 623/10; 128/92 W; 604/93; 604/891; 604/892
[58] Field of Search ............. 623/10; 128/92 C, 92 G; 604/93, 891, 892

[56] References Cited

U.S. PATENT DOCUMENTS 4,097,935 7/1978 Jarcho ..................................... 623/10
4,430,760 2/1984 Smestad ................................. 623/10

OTHER PUBLICATIONS

Frame et al., "Hydroxyapatite as a Bone Substitute in the Jaws," *Biomaterials,* 2, Jan. 1981, pp. 19-22.
*The Compendium of Continuing Education in Destistry,* Supplement No. 2, 1982, pp. S45-S85.
Cranin et al., "Human Mandibular Alviolar Ridge Augmentation with Hydroxylapatite a Four Year Analysis," 9th Annual Meeting of the Society for Biomaterials, Apr. 27-May 1, 1983, p. 25.
dePutter et al., "In Vivo Fatigue Behaviour of Permucosal Dental Implants of Calciumhydroxylapatite, Comparing Non-Prestressed with Prestressed Implants," 9th Annual Meeting of the Society for Biomaterials, Apr. 27-May 1, 1983, p. 27.
Niwa et al., "Preparation of Porous and Granule Hydroxyapatite and Possibility of Application as a Bone Graft," 9th Annual Meeting of the Society for Biomaterials, Apr. 27-May 1, 1983, p. 24.
Calcitek, Inc., "Calcitite Brand of Hydroxylapatite (Dense, Non-Resorbable) a New Solution for Alveolar Bone Restoration."
Calcitek, Inc., "Calcitite 2040 Nonresorbable Hydroxylapatite Bone Grafting Material for Alveolar Ridge Augmentation," Jun. 18, 1982.
Cook-Waite Laboratories, Inc., "Alveograf Brand of Durapatite (18-40 Mesh) Alveolar Ridge Bone-Grafting Implant Material," Jun. 1982.
Cook-Waite Laboratories, Inc., "A New, Nonresorbable Bone-Grafting Implant that Restores Alveolar Ridge Height and Width Permitting Denture Construction in a Matter of Weeks."
Miter, Inc., "Augmen a Synthetic Bone Grafting Material Which is Replaced by New Bone as it Resorbs-For Physiological Augmentation for Alveolar Ridges."
Misiek et al., "The Inflammatory Response to Different Shaped Hydroxylapatite Particles Implanted in Soft Tissue," 9th Annual Meeting of the Society for Biomaterials, Apr. 27-May 2, 1983, p. 23.
Jarcho, in "Calcium Phosphate Ceramics as Hard Tissue Prosthetics," *Clinical Orthopaedics,* 157, Jun. 1981, pp. 259-278.
Kranen et al., "The Use of Durapatite in Maxillofacial Reconstruction," 9th Annual Meeting of the Society for Biomaterials, Apr. 27-May 1, 1983, p. 26.
Mulliken et al., "Use of Demineralized Allogeneic Bone Implants for the Correction of Maxillocraniofacial Deformities," *Annals of Surgery,* 194, No. 3, Sept. 1981, pp. 366-372.

*Primary Examiner*—John Kight
*Assistant Examiner*—M. L. Moore
*Attorney, Agent, or Firm*—Wegner & Bretschneider

[57] ABSTRACT

A delivery system for implantation of fine particles in surgical procedures made of a collagen tube filled with the fine particles, the tube being made of a cast collagen film having holes in it larger than the size of the particles to allow cell migration. The system is particularly useful for alveolar ridge augmentation.

13 Claims, No Drawings

DELIVERY SYSTEM FOR IMPLANTATION OF FINE PARTICLES IN SURGICAL PROCEDURES

This application is a continuation of Ser. No. 649,281 filed Sept. 11, 1984, now abandoned.

BACKGROUND OF THE INVENTION

This invention relates to medical devices, in particular a delivery system for implantation of powders or fine particles in surgical procedures and, more particularly, this invention relates to an absorbable collagen tube or pouch for the containment of fine particles for surgical implantation. In a preferred embodiment, this invention relates to the aforementioned delivery system as used in dental surgery, that is, in alveolar ridge augmentation.

It is quite common for the bone of the mandible and the maxilla of older individuals to have resorbed during their lifetime to the extent that in the case of the mandible it is too thin and weak to support dentures and presents a high risk of fracture. In such instances of severely atrophic mandible or maxilla, procedures have been developed wherein the oral surgeon builds up the height and width of the alveolar ridge with autogenous cancellous bone or in more recent years by introducing non-resorbable hydroxylapatite or related resorbable tricalcium phosphate into a tunnel made in the periosteum covering the mandible or maxilla. It has been found that hydroxylapatite which makes up the bulk of the human skeletal system, ranging from approximately 65% of bone to 98% of dental enamel is biocompatible and well tolerated and in time becomes well bonded to the natural bone. New bone grows around and incorporates the particles of hydroxylapatite.

The usual procedure employed by the oral surgeon in placing the hydroxylapatite particles in close proximity to the mandibular or maxillary bone is to make a subperiosteal tunnel or pocket and with a delivery syringe introduce the fine particles of sterile hydroxylapatite or tricalcium phosphate alone or in combination with autogenous bone chips admixed with sterile saline. Although this procedure has been successful in augmentation of the alveolar ridge, it has certain limitations. The particles of hydroxylapatite or tricalcium phosphate lack form and cohesive strength and tend to migrate into the neighboring tissue and also are dislodged under externally applied forces. The syringe delivery system offers further limitations in particle placement. These prior art procedures are well-documented in the literature as, for instance, in Frame et al., "hydroxyapatite as a Bone Substitute in the Jaws," *Biomaterials*, 2, January 1981, pp. 19–22; *The Compendium of Continuing Education in Dentistry*, Supplement No. 2, 1982, pp. S45–S85; Cranin et al., "Human Mandibular Alviolar Ridge Augmentation with Hydroxylapatite a Four Year Analysis," 9th Annual Meeting of the Society for Biomaterials, Apr. 27–May 1, 1983, p. 25; dePutter et al., "In Vivo Fatigue Behaviour of Permucosal Dental Implants of Calciumhydroxylapatite, Comparing Non-Prestressed with Prestressed Implants," 9th Annual Meeting of the Society for Biomaterials, Apr. 27–May 1, 1983, p. 27; Niwa et al., "Preparation of Porous and Granule Hydroxyapatite and Possibility of Application as a Bone Graft," 9th Annual Meeting of the Society for Biomaterials, Apr. 27–May 1, 1983, p. 24; Calcitek, Inc., "Calcitite Brand of Hydroxylapatite (Dense, Nonresorbable) a New Solution for Alveolar Bone Restoration;" Calcitek, Inc., "Calcitite 2040 Nonresorbable Hydroxylapatite Bone Grafting Material for Alveolar Ridge Augmentation," June 18, 1982; Cook-Waite Laboratories, Inc., "Alveograf Brand of Durapatite (18–40 Mesh) Alveolar Ridge Bone-Grafting Implant Material," June 1982; Cook-Waite Laboratories, Inc., "A New, Nonresorbable Bone-Grafting Implant that Restores Alveolar Ridge Height and Width Permitting Denture Construction in a Matter of Weeks;" and Miter, Inc., "Augmen a Synthetic Bone Grafting Material Which is Replaced by New Bone as it Resorbs-For Physiological Augmentation of Alveolar Ridges." See also Misiek et al., "The Inflamatory Response to Different Shaped Hydroxylapatite Particles Implanted in Soft Tissue," 9th Annual Meeting of the Society for Biomaterials, Apr. 27–May 1, 1983, p. 23.

In addition to the forms of hydroxylapatite discussed above which are used for alveolar ridge augmentation, other form of hydroxylapatite, demineralized bone, and other similar materials have been used as prosthetic materials. U.S. Pat. No. 4,097,935 discloses a hydroxylapatite ceramic for use as a dental restorative composition and a prosthetic material. Calcium phosphate ceramics are also discussed as prosthetics by Jarcho, in "Calcium Phosphate Ceramics as Hard Tissue Prosthetics," *Clinical Orthopaedics*, 157, June 1981, pp. 259–278. See also Kranen et al., "The Use of Durapatite in Maxillofacial Reconstruction," 9th Annual Meeting of the Society for Biomaterials, Apr. 27–May 1, 1983, p. 26; and Mulliken et al., "Use of Demineralized Allogeneic Bone Implants for the Correction of Maxillocraniofacial Deformities," *Annals of Surgery*, 194, No. 3, September 1981, pp. 366–372.

The main problems associated with the use of powdered hydroxylapatite, tricalcium phosphate, autogenous cancellous bone, or demineralized bone for alveolar ridge augmentation are the migration of the mineral powder and the resorption of the powder. There is also the possibility of an inflamatory response based on the shape of the particles. There has been an attempt at solving some of these problems by encapsulating the particles in a casing made of a woven or non-woven fabric. This is disclosed in U.S. Pat. No. 4,430,760 which issued to Thomas L. Smestad on Feb. 14, 1984. The Smestad patent, teaches the use of cancellous or compact bone, or dentin, which has been comminuted to a particle size in the range of about 40 to 500 microns and contained within a "porous" casing which is a woven or non-woven fabric. Typical woven fabrics are Dacron, Nylon, and Carbon fabrics. Typical non-woven fabrics are disclosed as being made of collagen, polyesters, polyamides, and polyolefins. It is a requirement of the Smestad invention that the maximum pore size of the fabric is less than the smallest particles size of the bone or dentine powder. There is a disadvantage associated with the use of the woven and non-woven fabrics, namely, the synthetic polymers used are not bioerodible. In addition, it is clear from the disclosure of the Smestad Patent that all the fabrics used are microporous. The pore size is too small to allow migration of cells into the package. Thus, the Smestad prosthesis suffers from the same disadvantages as the other prior art techniques.

SUMMARY OF THE INVENTION

It is, therefore, the primary object of the present invention to provide a delivery system for implantation of fine particles for surgical implantation which is free of the aforementioned and other such disadvantages.

It is another object of the present invention to provide an absorbable collagen tube containing particles of hydroxylapatite or other suitable particulate materials useful for augmenting the alveolar ridge.

It is still another object of the present invention to provide a method of augmenting the alveolar ridge by implantation of an absorbable collagen tube containing particles of hydroxylapatite or other suitable particulate materials.

It is yet another object of the present invention to provide a method of making an absorbable collagen tube or pouch containing particles of hydroxylapatite or other suitable particulate materials for use in alveolar ridge augmentation or for bone augmentation in orthopedic and reconstructive surgery.

Consistent with the foregoing objects, a delivery system for implantation of fine particles in surgical procedures comprising a collagen tubular device filled with the particles, the collagen tube comprising a cast collagen film having a plurality of perforations therein, the perforations being larger than the size of the particles, and the tube being sealed at both ends, is provided. In the preferred embodiment, the fine particles are either powdered or particulate hydroxylapatite, tricalcium phosphate, autogenous cancellous bone, demineralized bone, or mixtures thereof and have a particle size in the range of from about 20 mesh to about 200 mesh (about 74 microns to about 840 microns). The preferred particle size distribution can be about 20 to about 40 mesh (about 400 to about 800 microns) or about 40 to about 60 mesh (about 250 to about 400 microns) depending on the preference of the surgeon and on the conditions found to exist in the patient.

It has already been mentioned that the use of hydroxylapatite, tricalcium phosphate, etc. as an implant is already known. What is important to the present invention is the containment of the particulate matter in a collagen tube having certain characteristics. As used herein, "tube" is meant to encompass both a tube and a pouch.

Collagen is a fibrous protein and constitutes the major protein component of skin, bone, tendon, ligament, cartilage, basement membrane and other forms of connective tissue. It is the most abundant protein in the animal kingdom. In bone, collagen fibers reinforce the calcium phosphate mineral base. Despite its great strength bone retains flexibility because of its collagen content.

Collagen has use in medicine and in surgery. Collagen based devices have use as sutures, hemostatic fiber and sponges, wound dressings, neurosurgical sponges, injectable implants for soft tissue augmentation, pharmaceutical carriers, nerve regeneration conduits, ophthalmic aqueous-venous shunts, contact lenses and others.

The properties of collagen which favor its use as a biomaterial are many. It has a high order of tensile strength and low extensibility. Collagen is biodegradable, and when implanted in the body, is absorbed at a rate that can be controlled by the degree of intra or intermolecular crosslinking imparted to the collagen molecule by chemical or physical treatment. One can thus design collagen products which, on implantation, will be completely absorbed in a few days or in months. One can chemically treat collagen so that it becomes totally non-absorbable while still retaining its hydrophilic character and its good tissue response. Although native collagen is a very weak antigen, it can be made for all practical purposes, immunologically inert.

The collagen molecule is a triple helix and has a unique protein conformation that is a coiled coil of three polypeptide subunits or alpha chains. Each alpha chain twists in a left-handed helix with three residues per turn, and three chains are wound together in a right-handed superhelix to form a rod-like molecule about 1.4 nanometers in diameter and 300 nanometers long. The alpha chains each contain about 1,050 amino acid residues and the molecular weight of the collagen molecule is, therefore, about 300,000. In each alpha chain within the triple helix every third amino acid residue is glycine. Collagen is characterized by a high content of proline and hydroxyproline amino acids, the absence of tryptophane, minor amount of aromatic amino acids, and a significant amount of dicarboxylic and dibasic amino acids. At both ends of the collagen molecule there are terminal peptide sequences known as telopeptides which are not triple helical in structure and which lack glycine at every third residue. The telopeptides are the primary sites of internal cross-linking in the molecule and are the most antigenic portions of the collagen molecule. The collagen molecule which is elaborated by fibroblast cells aggregate in the extracellular matrix of connective tissue to form fibrils which range from 10 to 200 nanometers in diameter. The collagen fibrils aggregate into collagen fibers.

The main sources of collagen for commercial application are bovine tendon, calf, steer or pig hide. All are readily available at relatively low cost. Reconstituted collagen products are prepared by purification of native collagen by enzyme treatment and chemical extraction. The purified collagen is dispersed or dissolved in solution, filtered and retained as such, or is reconstituted into fiber, film or sponge by extrusion, casting or lyophilization techniques.

Finally, although the collagen of skin, tendons, bone, cartilage, blood vessels and basement membrane are similar in structure and composition, they do differ slightly in relative amino acid content, amino acid sequence and in architecture. They are products of different genetic loci. The different genetic collagens are known as Type I, II, III, IV, V, etc. The collagen of native skin, tendons, ligaments and bone are primarily Type I collagen.

In making the collagen tube to contain the fine particles, a collagen dispersion is first prepared in a manner well-known in the art. One such preparation procedure is taught in U.S. Pat. No. 3,157,524 which is embodied herein in its entirety by reference. Attention is particularly directed to Example I of that patent. Another preparation of collagen is taught, for instance, in U.S. Pat. No. 3,520,402 which is embodied herein in its entirety by reference.

After the collagen dispersion is prepared, a film is cast on a mandrel by pouring the collagen dispersion over the revolving mandrel while, at the same time, precipitating the collagen to thereby coat the mandrel. After pressing excess water from the cast film, it is washed and dried. The tube is then removed from the mandrel. While the shape of the mandrel in the preferred embodiment is such as to form a tubular collagen container, the shape of the mandrel can be chosen to result in a device having any desired shape. Thus, for instance, the mandrel can be in the shape of a patient's chin to make an artificial chin implant, the resulting collagen pouch being perforated and filled with the hydroxylapatite, or the like.

After removal from the mandrel, the tube is perforated in a known manner to provide the necessary holes for the migration of cells into the implanted package. The holes are in the range of about 4 to about 40 mils (about 100 to about 1,000 microns) and, preferably one about 20 mils (about 500 microns) in diameter. In addition, if a crimped collagen is desired, the tube is placed on a mandrel and wetted after which the ends are pressed toward each other thus crimping the tube.

Whether or not the tube is crimped, it must be cross-linked after being perforated. If the tube is crimped, the cross-linking is done after crimping. Again, cross-linking is performed in a manner well-known in the art such as by treatment with an aldehyde as, for example, formaldehyde or glutaraldehyde.

After these pre-treatments, the tube is packed with the fine particles by sealing one end, filling the tube with the particles, and then sealing the other end. The filled tubes are then sterilized using known techniques.

DETAILED DESCRIPTION OF THE PREFERRED EMBODIMENTS

The collagen used in the instant invention is, as already mentioned, prepared in a conventional manner. A specific method of preparation, which is exemplary only and is not to be taken as limiting, is described in Example 1.

EXAMPLE 1

Preparation of Collagen Dispersion

Bovine deep flexor tendon, freshly harvested, is mechanically cleaned of fat, fascia and other extraneous matter and is washed with sodium dodecyl sulfate detergent solution. The tendon is frozen and sliced across the fiber axis with a meat slicer to give slices of approximately 0.4 mm thickness. Six hundred grams of tendon slices is added to a solution of 25 gm potassium dihydrogen phosphate and 1 gm sodium hydroxide in 5 liters of demineralized water warmed to 37° C. The pH is adjusted to 6.15±0.15 and a solution of 4.7 gm of the enzyme Ficin in 50 ml water is added. The mixture is maintained at 37° C. and allowed to stand for one hour with intermittent stirring. At the end of this period the liberated fat is skimmed off the surface and the slices removed and washed with water. The tendon slices are then placed in a solution of 50 gm ammonium nitrate and 5 gm sodium chlorite in 5 liters of water and the mixture agitated for one hour. The slices are removed and washed well with water. A sample of the treated slices is taken for a percent solids determination.

One hundred grams of the enzyme treated slices (approximately 20% dry weight) is dispersed in a solution of 2700 ml water containing 6 gm of 85% lactic acid and the mixture is homogenized in a Waring Blendor. The temperature is not allowed to rise above 30° C. The collagen dispersion is then filtered through a 100 mesh stainless steel screen and is deaired under vacuum.

Once the collagen dispersion is prepared, the tubes are made by casting a film of the collagen. The procedure, described in Example 2, is exemplary of one such method of preparation.

EXAMPLE 2

Preparation of Collagen Tubes

Onto a revolving mandrel consisting of a 1 cm glass tube 8 inches long coated with aluminum foil is slowly poured simultaneously 100 ml of a collagen dispersion (0.7% solids) and 200 ml of a 1% ammonia solution. The precipitated fibrous collagen is allowed to coat the mandrel evenly. The collagen coated mandrel is pressed against the inside of a glass test tube to squeeze out liquid and is briefly washed with ethanol. The collagen tube is allowed to dry on the mandrel before it is removed.

Once the collagen tube has been made, it is then perforated.

EXAMPLE 3

Preparation of Perforated Collagen Tube

Enzyme treated tendon slices (11.35 gm) were swelled in a solution of 3.3 gm 85% lactic acid in 412 ml deionized water. The mixture was homogenized in a Waring Blendor for 20 seconds, methanol (110 ml) was added and the dispersion was again blended for 20 seconds. The dispersion was filtered through 100 mesh stainless steel screen and was deaired under vacuum. A portion of this dispersion (75 ml) was poured slowly and simultaneously with a 1% ammonia solution (75 ml) onto a revolving mandrel consisting of a steel rod covered with polyethylene tube 5 mm in diameter and 8 inches long. The collagen coating was pressed to squeeze out water, washed with ethanol and air dried. The collagen tube was removed and was perforated with 20 mil holes spaced 3/16" apart with steel tube punches.

EXAMPLE 4

Preparation of a Crimped Collagen Tube

A perforated 5 mm diameter 6 inch collagen tube as prepared in Example 3 was placed on a 5 mm steel rod and was wetted with a 50% ethanol solution. The ends of the tube were pressed toward each other thus crimping the tube and diminishing the length of tube to 2 inches. The ends of the crimped tube were held in place until the tube was dried.

EXAMPLE 5

Crosslinking of Collagen Tube

Ten perforated collagen tubes 8 mm diameter 6 inch lengths were placed into a solution of 16.5 ml of 37% formaldehyde and 20 gm of sodium bicarbonate in 2 liters of water and allowed to sit at room temperature for 15 minutes. The tubes were removed, washed with deionized water and dried.

EXAMPLE 6

Crosslinking of Collagen Tubes

Ten perforated and crimped collagen tubes 5 mm diameter 6 inch lengths were placed into a solution of 12.5 ml of 8% glutaraldehyde and 20 gm sodium bicarbonate in 2 liters of deionized water and allowed to sit at room temperature for 5 minutes. The tubes were removed and washed successively with deionized water and isopropyl alcohol and then dried.

EXAMPLE 7

Preparation of Collagen Tubes Filled with Hydroxylapatite

The collagen tubes of the above examples were briefly moistened at one end and the end was tied with a 4-0 catgut chromic suture. The tubes were packed with hydroxylapatite 40-60 mesh and the other end tied similarly with a catgut suture. The packed collagen tubes of lengths varying from 3 cm to 12 cm were sterilized by cobalt irradiation.

Having considered the preparation of the filled collagen tubes, attention is now directed to the following example describing animal tests made to compare the device of the present invention with hydroxylapatite alone.

EXAMPLE 8

Thirteen male outbred albino spragan Dawley rats 4 to 8 months of age were used as experimental animals. The graft site chosen was a circular ovoid transosseus defect (including lateral and medial periosteum) in the angle of the mandible.

The hydroxylapatite used in this study was of small particle size (40-60 mesh) irregularly shaped crystals, PERIOGRAF (Cooke Waite Laboratories, Inc.), and the large size (20-40 mesh) rounded crystals, Calcitite (Calcitek, Inc.).

The animals were divided into two groups, a study group, n=10, and a control group, n=3. The animals were anesthetized with Ketamine Hydrochloride (100 mg/kg) injected intraperitoneally and supplemented with local infiltration of 2% Xylocaine into the operative area. In the study group both angles of the mandible were exposed. Round to oval transosseus defects were made through the bone including lateral and medial periosteum. Diameters ranged from 5-7 mm. The wounds were irrigated with saline prior to placement of the grafts. On the right side approximately 300 mg of hydroxylapatite of selected particle shape and size, contained in a collagen tube, was placed in the transosseus boney defect. On the left side a similar amount of the hydroxylapatite material, not within a collagen container, was placed with a spoon excivator or a syringe directly into the osseous defect. In the control group the transosseus defects were prepared in a similar fashion to the study group. On the right side a collagen tube without particulate matter was placed into the transosseus defect. On the left side the boney defect was left ungrafted and allowed to heal spontaneously. Selected animals were sacrificed at 4-8, and 16 weeks and their mandibles dissected. All graft sites were examined and a comparison was made between the right and left sides. Clinical, radiographic, and histologic data were included in the evaluation.

In the control animals no osseous healing was seen in the ungrafted defect on the left side at 8 and 16 weeks. On the right side where the collagen tube was placed, there was no evidence of persistance of the collagen material at 8 or 16 weeks. There was no evidence of osseous induction or osseous healing.

At 4-8, and 16 weeks on the right side where the collagen tube containing hydroxylapatite particles was used the grafts were detected as a round, and firm elevation on the lateral and medial surface of the mandible angle. On the left side where hydroxylapatite particles alone were implanted, the defects in two animals healed in a similar fashion to the right side. The remaining 8 left side implants appeared as a firm simicircular consolidation on only the lateral aspect of the mandibular angle at the inferior aspect of the circular graft site.

Radiographic results confirm the clinical findings. All collagen tube grafts showed a dense consolidate of graft material within the entire transosseus defect. On the opposite side where no collagen container was used, two implants which clinically resembled the collagen carrier side showed radiographic evidence of complete fill of the transosseus defect by hydroxylapatite particles. In the remaining left side sites, however, there was a half circular consolidation of hydroxylapatite particles at the inferior aspect of the defect. Additionally in all of the non-collagen graft sites there was radiographic evidence of graft material in areas outside of the intended transosseus graft site.

On histologic examination it was found that on the collagen container side there was evidence of persistance of the collagen material at 4 weeks and none in evidence at 8 and 16 weeks. There was in all specimens examined little to no osteoplastic response throughout the study period. The character of cellular response was primarily fibroblastic with macrophaages and giant cells present.

The results of this experiment showed that an absorbable collagen tube can be used as a container, to place particulate hydroxylapatite bone substitute material into a pocket in the periosteum without significantly affecting the favorable properties of the graft material. The collagen container provided support for the hydroxylapatite particles for up to four weeks. Operative placement was simplified with little spillage of graft material into undesired areas.

In addition to the animal tests, a number of clinical tests were made. The procedures followed are set forth below.

EXAMPLE 9

Mandibular Ridge Augmentation

The patient was a 50 year old white female with a history of wearing a mandibular partial denture for more than twenty years. Radiographic and clinical evaluation showed her mandible to be no more than 8 mm fixed bilaterally in the body region. No more than 2 mm of attached gingiva were present at the crest of the ridge and tissue overlying the mandible intraorally was composed of mobile mucosa with high muscle attachments. The patient was referred by her private dentist who stated that he had been unable to fabricate a satisfactory lower removal appliance for her. She was subsequently scheduled for the first stage of mandibular reconstruction consisting of an alloplastic mandibular ridge augmentation.

Procedure: The patient was brought to the Operating Room and placed on the operating table in the supine position. The patient was sedated with Fentanyl and Diazepam and then prepared in the usual fashion for intraoral surgery. Local anesthesia was then administered consisiting of 7 cc of 2% Lidocaine with 1:100,000 parts Epinephrine. Following satisfactory induction of local anesthesia and once adequate time had been allowed for hemostasis, a partial thickness mucosal incision was made just posterior to the right mandibular cuspid tooth. This incision was approximately 1 cm long and extended from the crest of the ridge laterally into the buccal vestibule. A submucosal dissection was then carried along the crest of the ridge to the retromolar region using Metzenbaum scissors. The wound margins were then retracted in the buccal vestibule and the mental nerves isolated using blunt dissection. The nerve was then retracted inferiorly and a periosteal incision made thorugh the previous mucosal incision. The periosteum was then elevated along the crest of the mandible using the Freer elevator. Care was taken not to extend the periosteal stipping over the lateral border of the mandible or across the lingual crest of the ridge. Once this had been accomplished, this wound was packed with moist gauze and attention directed to the left side of the mandible. An identical incision was made through mucosa in the left cuspid region just posterior to the cuspid tooth and into the vestibule. The submucosal and subperiosteal dissections were carried out in an identical fashion to the right side. The mental nerve was noted to be in a slightly superior position on the left side and again it was retracted inferiorly and protected during the dissection. Once this had been accomplished, the synthetic hydroxylapatite was prepared in the special injection syringe. The periosteum was then retracted using the Freer elevator and the syringe inserted into the tunnel at the crest of the ridge which had been created by the dissection. The material was then injected subperiosteally with attention taken to assure that it remained on the crest of the mandibular ridge. 3 gm of hydroxylapatite were injected in this fashion on the right side. Once this had been accomplished, the wound was closed using #4-0 Vicryl interrupted horizontal mattress sutures. Attention was then directed to the left side of the ridge where again the periosteum was retracted in preparation of insertion of the graft. For this side, a collagen tube, 5 mm in diameter, was filled with 4 gm of hydroxylapatite. The tube was ligated with a #0 chromic suture. A large GI needle was inserted beneath the mucosa at the crest of the mandible and brought out just inferior to the retromolar pad. This suture was used to pull the collagen tube filled with hydroxylapatite into the mubmucosal tunnel at the crest of the mandibular alveolus. The suture was then cut level with the mucosa, the wound irrigated and a small additional amount of hydroxylapatite material packed into the region of the incision. The wound was then closed using #4-0 interrupted horizontal mattress sutures with Vicryl. The mouth was irrigated and the patient was taken to the Recovery Room in satisfactory condition. The patient tolerated the procedure well.

On examination three weeks post-operatively, the ridge on the left side in which the collagen tube filled hydroxylapatite was placed, was nicely rounded. The material appeared to be very well tolerated.

EXAMPLE 10

The patient was diagnosed as having mandibular and maxillary atrophy. The patient had a history of progressive difficulty eating secondary to severe atrophy of the alveolar process on both the maxilla and the mandible. She was scheduled for maxillary and mandibular augmentation with hydroxylapatite.

Procedure: The patient was brought to the operating room and placed on the table in the supine position. Excellent anesthesia was obtained via nasal endotracheal intubation. The patient was prepped and draped in the usual fashion for an intraoral procedure, and approximately 9 cc of 1% Lidocaine with 1:100,000 Ephinephrine was infiltrated into the oral mucosa overlying the anterior maxilla and posterior mandible bilaterally.

Attention was first directed to the left posterior mandibular segment, where a 1 cm incision was made on the alveolar ridge lateral to the crest in the first premolar region. This incision was made just below the mucosa and using a curved Metzenbaum scissor, a submucosal tunnel was made above the level of the periosteum along the crest of the alveolar ridge to the retromolar region. An incision was then made with a #15 scapel blade through the periosteum and a similar tunnel was made on the crest of the alveolar ridge to the retromolar area again. Approximately 9 grams of 18 to 40 mesh hydroxylapatite was injected into the subperiosteal tunnel. Care was taken to avoid trauma to the mental nerve which exited near the incision site. Following the placement of adequate graft material, the wound was closed using horizontal mattress sutures of 4-0 Vicryl, and oversewn with running interlocking sutures of 4-0 Vicryl.

An identical procedure was performed on the contralateral side, except that in the anterior segment a small amount of collagen tube was used to contain the graft material near the incision. The wound was again closed with a double layer of 4-0 Vicryl sutures.

Attention was then directed to the maxilla, where two incisions were made, one buccal to the first premolar region on the upper right and another identical incision on the upper left. Again submucosal tunnels were made following the form of the atrophied arch and connecting the two incisions. The periosteum was then sharply divided and a subperiosteal tunnel was created along the route of the previously created submucosal tunnel. Using a 5 mm diameter collagen tubing packed with hydroxylapatite, the anterior maxilla was reconstructed with an approximately 5 cm long length of graft material. The graft was inserted in one incision and drawn around to the other incision using a tonsillar hemostat. Hydroxylapatite was then injected around the graft to fill in the defects and placed in the buttress regions as well. The wounds were closed with horizontal mattress sutures of 4-0 Vicryl and oversewn with running interlocking stitch of 4-0 Vicryl. The mouth ws then thoroughly irrigated and suctioned free of debris. The previously placed gauze throat pack was removed, and the oropharynx was suctioned free of blood and debris.

EXAMPLE 11

The patient was diagnosed as having severe mandibular atrophy. She was scheduled for augmentation of the mandibular alveolar ridge with hydroxylapatite.

Procedure: Under excellent nasoendotracheal anesthesia, the patient was surgically prepared with Betadine and sterilely draped. Approximately 6 cc. of one percent Xylocaine with Epinephrine 1:100,000 ws infiltrated subperiosteally on the mandibular ridge. A saline moistened pharyngeal pack was placed. With a #15 scalpel blade, a 1 cm incision was made just anterior to the mental foramen at the right angle to the alveolar ridge. With small Metzenbaum scissors a supraperiosteal pocket was made running posteriorly to the ascending ramus. The mental nerve was identified and carefully retracted. An incision through the periosteum was made with the scalpel and a subperiosteal pocket overlying the superior border of the mandible was made with a Freer periosteal elevator. Six tubes of Alveograf brand Hydroxylapatite (each 0.75 grams) were carefully placed subperiosteally to enhance the ridge. In the anterior of the mandible a similar pocket was created and a 5 mm diameter×3.5 cm long tube of collagen filled with Hydroxylapatite was carefully positioned. An incision undermining the left side of the mandible and placement of Hydroxylapatite was performed in the same manner as on the right. A total of 16 tubes each containing 0.75 grams of Hydroxylapatite was used to augment the mandible. The two incisions were closed with 4-0 Vicryl in a double suture, one a multiple interrupted suture closure and one with a running suture. Estimated blood loss was nil. Copious irrigation with saline was carried out and throat pack removed. The patient was taken to the Recovery Room in satisfactory condition.

It should be apparent from the foregoing detailed description that the objects set forth herein above have been successfully achieved. Moreover, while there are shown and described present preferred embodiments of the invention it is to be distinctly understood that the invention is not limited thereto but may be otherwise variously embodied and practiced within the scope of the following claims. Accordingly,

What is claimed is:

1. A delivery system for implantation of fine particles in surgical procedures comprising a collagen tube or pouch filled with said particles, said collagen tube or pouch comprising a cast collagen film having a plurality of perforations therein, said perforations being larger than the size of said particles, said tube or pouch being sealed.

2. A delivery system as claimed in claim 1, wherein said fine particles comprise a member of the group consisting of powdered or particulate hydroxylapatite, tricalcium phosphate, autogenous cancellous bone, demineralized bone, and mixtures thereof.

3. A delivery system as claimed in claim 2, wherein said fine particles have a particle size of from about 70 microns to about 850 microns.

4. A delivery system as claimed in claim 3, wherein said particles have a particle size in the range of about 400 microns to about 850 microns or in the range of about 250 microns to about 400 microns.

5. A delivery system as claimed in claim 3 or 4, wherein said perforations are at least about 100 microns.

6. A delivery system as claimed in claim 5, wherein said perforations are from about 100 microns to about 1,000 microns.

7. A delivery system as claimed in claim 6, wherein said perforations are about 500 microns.

8. A delivery system as claimed in claim 1, wherein said collagen tube or pouch is a tube and is crimped.

9. A delivery system as claimed in claim 1 or 5, wherein said collagen is cross-linked.

10. A method of augmenting the alveolar ridge comprising making an incision in a predetermined location in the area of the alveolar ridge, inserting a delivery system which comprises a collagen tube filled with particles of hydroxylapatite, tricalcium phosphate, autogenous cancellous bone, demineralized bone, or mixtures thereof, having a particle size of from about 70 microns to about 850 microns, said collagen tube being made of a cast collagen film and having a plurality of perforations of at least about 150 microns in size and larger than the size of said particles, and closing said incision.

11. A method of making a delivery system, for implantation of fine particles in surgical procedures comprising casting a collagen film tube or pouch, making a plurality of perforations of a size larger than the particle size of said fine particles, in said tube or pouch, and filling said tube or pouch with said fine particles.

12. A method as claimed in claim 11, wherein said particle size is from about 70 to about 850 microns and said perforations are about 100 to about 1,000 microns.

13. A method as claimed in claim 11, wherein said cast collagen film tube or pouch is made by pouring a dispersion of collagen over a revolving mandrel while, simultaneously, precipitating said collagen from the dispersion.

* * * * *